United States Patent [19]

Schultz et al.

[11] Patent Number: 5,763,249
[45] Date of Patent: Jun. 9, 1998

[54] ANTIBODY-MEDIATED REDUCTION OF α-KETOAMIDES

[75] Inventors: Peter G. Schultz, Oakland; Mark A. Gallop, East Palo Alto, both of Calif.

[73] Assignee: The Regents of the University of California, Oakland, Calif.

[21] Appl. No.: 805,502

[22] Filed: Dec. 9, 1991

[51] Int. Cl.$^6$ .................................................. C12P 13/02
[52] U.S. Cl. ..................... 435/188.5; 435/128; 435/129; 530/388.9
[58] Field of Search ........................... 530/388.1, 388.9; 435/188.5, 128, 129

[56] References Cited

U.S. PATENT DOCUMENTS 4,659,567  4/1987  Tramontano et al. ............... 424/85.8
4,888,281  12/1989  Schochetman et al. ............ 530/388.9

*Primary Examiner*—Toni R. Scheiner
*Attorney, Agent, or Firm*—Townsend and Townsend and Crew LLP

[57] ABSTRACT

Monoclonal antibodies raised against a 4-nitrophenyl phosphonate hapten catalyze the stereospecific reduction of an α-ketoamide to the corresponding α-hydroxyamide in the presence of an appropriate reducing agent.

3 Claims, No Drawings

ANTIBODY-MEDIATED REDUCTION OF α-KETOAMIDES

This invention lies in the field of the use of antibodies as catalysts in chemical reactions.

This invention was made with Government support under Contract No. DE-AC03-SF-00098 awarded by the Department of Energy. The Government has certain rights in this invention.

BACKGROUND AND SUMMARY OF THE INVENTION

The development of catalytic enantioselective reactions for the synthesis of pure chiral compounds has become an important focus of synthetic organic chemistry. By virtue of their remarkable specificities, enzymes are being used in an increasing number of applications. Unfortunately, only a limited number of enzymes are available for this type of use, and in many cases the use of an enzyme makes it difficult to retrieve a necessary cofactor from the reaction mixture for reuse. As alternatives to enzymes, synthetic chiral catalysts have been developed for epoxidation, hydrogenation, and the reduction of keto acids and aromatic and α,β,-unsaturated ketones and aldehydes. A third alternative for enantioselective catalysts is the use of immunological receptors, but the use of such receptors is still at a very early stage.

It has now been discovered that certain novel immunological receptors are useful in catalyzing the stereospecific reduction of 1-(p-nitrobenzyl)-2-(α-methyl-benzylamino) ethanedione and similar α-ketoamides to the corresponding α-hydroxyamides in the presence of a suitable reducing agent such as sodium cyanoborohydride. These receptors are preferably monoclonal antibodies raised against haptens which are similar in formula to the α-ketoamide except that the α-carbonyl group of the α-ketoamide is replaced in the hapten by a phosphonate moiety. This discovery suggests that by the use of appropriately selected monoclonal antibodies, whose means of selection will be apparent from this disclosure, chiral alcohols and amines can also be prepared in a stereospecific manner.

DETAILED DESCRIPTION OF THE INVENTION AND PREFERRED EMBODIMENTS

Monoclonal antibodies for use in the practice of this invention are obtained in accordance with conventional procedures utilizing immunization, hybridization and hybridoma screening procedures well known among those skilled in the art. The hapten is for example conjugated to conventional carrier proteins through conventional linkages for use in immunization. The screening of the monoclonal antibodies to select those which catalyze the reaction toward the desired enantiomer may be achieved by using the antibodies in test reactions and analyzing the product of each to determine its stereospecificity. The success of the hapten in generating the appropriate antibodies suggests the following:

(1) the negatively-charged tetrahedral phosphonate moiety in the hapten induces the formation of an antibody combining site capable of polarizing a carbonyl group for attack by a hydride reagent;

(2) the antibody combining site provides a chiral environment that discriminates the transition states arising from the attack of hydride on the two faces of the carbonyl group;

(3) the conjugation of hapten to carrier protein at or near the phosphonate group insures the accessibility of a relatively small reductant to the carbonyl group;

(4) inhibition should be minimized by the use of the phosphonate group; and (5) the antibody-substrate interaction in systems of the type to which this invention relates exists independently of the transition state geometry.

The following example is offered for purposes of illustration, and is intended neither to limit nor to define the invention in any manner.

EXAMPLE

This example illustrates the use of the present invention in performing the reduction of 1 to 2S below, using monoclonal antibody raised against the hapten 3:

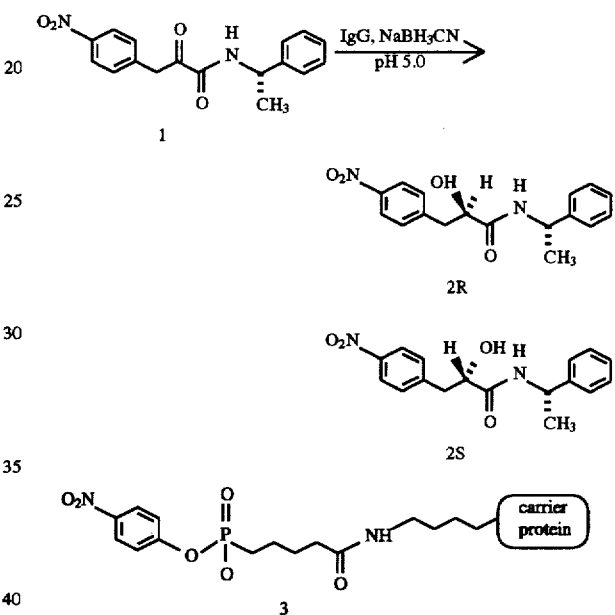

Monoclonal antibodies specific for the phosphonate 3 were purified to homogeneity by chromatography on protein-A coupled sepharose, as determined by polyacrylamide gel electrophoresis. Eight of these antibodies were assayed for their ability to reduce the ketoamide 1 by high performance liquid chromatography (HPLC). The (S)-(—)-α-methylbenzylamine group was incorporated into the ketoacid substrate to facilitate analysis of reaction specificity, it having previously been shown that antibodies specific for the phosphonate 3 are relatively insensitive to substitutions in the aliphatic linker. The ketoamide 1 was prepared by a modification of the method of Westerberg and coworkers (Westerberg, D.A., et al., J. Med Chem. 1989, 32, 236) for the preparation of 4-nitrophenylpyruvic acid. Two of the eight antibodies were found to catalyze the reduction of the ketoamide 1 to the α-hydroxyamide 2. One of these, an antibody defined herein as A5, was examined in greater detail.

The antibody-catalyzed $NaBH_3CN$-dependent reduction displayed a pH optimum at acidic pH. Consequently, all kinetic parameters were measured in the presence of 13μM antibody, 1mM $NaBH_3CN$ at 22° C in 50mM NaCl, 50mM MES buffer. Stock solutions of 1 (5mM) and 10μL $NaBH_3CN$ (50mM) were added to 0.5mL total volume of reaction buffer containing 2mg/mL antibody and 10%

(volume basis) methanol. Initial reaction rates were determined by measuring the amounts of 1 and 2 (both diastereomers) relative to a p-cresol internal standard using analytical reverse-phase HPLC (Rainin CYNAMAX MICROSORB $C_{18}$, a common silica-$C_{18}$ HPLC column packing, with a continuous phase consisting of 40–80% of TFA/$CH_3CN$ in 0.1% aqueous TFA).

The antibody A5 demonstrated saturation kinetics: a Lineweaver Burk analysis of the steady state kinetic data afforded a $K_{cat}=0.104min^{-1}$ and $K_m=1.24mM$. Greater than 25 turnovers were measured with no apparent change in $V_{max}$. The pseudo first-order rate constant for the uncatalyzed reaction ($k_{uncat}$) was found to be $3.6\times10^{-4}min^{-1}$. The antibody-catalyzed reaction was also inhibited by 4-nitrophenyl methylphosphate: the $K_d$ was determined from fluorescence quenching experiments to be 0.61µM.

The diastereomeric excess of the reaction was determined by extraction of product into methylene chloride followed by acetylation with acetic anhydride/DMAP and subsequent analysis using capillary gas chromatography. This was done by first adding stock solutions of 20µL of 1 (5mM) and 10µL $NaBH_3CN$ (50mM) in methanol to 0.5mL total volume of 10mg/mL antibody containing 10% (volume basis) methanol and shaking the resulting mixture for 4 hours. The mixture was then extracted with methylene chloride and the solvent removed. The resulting residue was dissolved in $CH_3CN$ and acetylated with acetic anhydride, pyridine and DMAP. The acetylated products were purified by reverse-phase HPLC (Rainin cynamax microsorb $C_{18}$, 30–80% of 0.06% of TFA/$CH_3CN$ in 0.1% aqueous TFA) prior to analysis by capillary GC (HP-1, crosslinked methyl silicone gum, 25m×0.2mm×0.33µM filn thickness), using N-(S)-(—)-methylbenzyl-(O)-acetyl- (S)-(—)-3-phenyllactamide as an internal standard. The diastereomeric excess of the antibody-catalyzed reaction was corrected for background reaction.

Product stereochemistry was assigned by comparison to authentic products, prepared as follows. The enantiomer N-(S)-(—)-methylbenzyl-O-acetyl- R-(+)-3-(4-nitrophenyl)-lactamide (2R) was prepared from R-3-(4-nitrophenyl)-lactic acid by condensation of the NHS ester with (S)-(–)-µ-methylbenzylamide followed by acetylation and chromatography on silica gel ($CH_2Cl_2$/ethylacetate). Sodium borohydride reduction of the ketoamide 1 afforded the product 2S (as a mixture of 2R and 2S).

Controls demonstrated product stereochemistry to be stable to the workup and assay conditions. The uncatalyzed reaction afforded α-hydroxyamide 2R with a diastereomeric excess of 55.7%. In contrast, antibody A5 afforded the product 2S with a diastereomeric excess of 99.2%. Note that this is opposite the stereospecificity of the uncatalyzed reaction, indicating that the antibody-combining site discriminates the enantiomeric transition states for carbonyl reduction with high selectivity. Further screening is expected to provide antibodies with a broad array of selectivities including specificity for the product 2R.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

What is claimed is:

1. A method for performing a stereospecific reduction reaction of an α-ketoamide to an α-hydroxyamide, said method comprising:
    (a) contacting in a reaction mixture the following species:
        (i) said α-ketoamide,
        (ii) a reducing agent, and
        (iii) monoclonal antibody raised against a hapten comprising an analog of said α-ketoamide in which the α-carbonyl group of said α-ketoamide is replaced by a phosphonate moiety, said monoclonal antibody having been screened on the basis of its catalytic activity toward said reduction reaction and
    (b) recovering said α-hydroxyamide from said reaction mixture.

2. A method in accordance with claim 1 in which said α-ketoamide is 1-(p-nitrobenzyl)-2-(α-methylbenzylamino) ethanedione.

3. A method in accordance with claim 1 in which said reducing agent is sodium cyanoborohydride.

* * * * *